US010071067B2

(12) United States Patent
Kaufmann et al.

(10) Patent No.: US 10,071,067 B2
(45) Date of Patent: *Sep. 11, 2018

(54) ANISE FLAVORED MEDICATION

(71) Applicant: The Procter & Gamble Company, Cincinnati, OH (US)

(72) Inventors: Allyn Michael Kaufmann, Morrow, OH (US); James Carl Grimm, Mason, OH (US); Chelsay Lynn Brewster, Fairfield Township, OH (US); Thomas Edward Huetter, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/807,668

(22) Filed: Nov. 9, 2017

(65) Prior Publication Data

US 2018/0064661 A1  Mar. 8, 2018

Related U.S. Application Data

(63) Continuation of application No. 15/247,955, filed on Aug. 26, 2016, now Pat. No. 9,839,620, which is a (Continued)

(51) Int. Cl.
*A61K 31/137* (2006.01)
*A61K 47/08* (2006.01)
(Continued)

(52) U.S. Cl.
CPC .......... *A61K 31/137* (2013.01); *A61K 9/0053* (2013.01); *A61K 9/0095* (2013.01); *A61K 9/08* (2013.01); *A61K 31/138* (2013.01); *A61K 31/167* (2013.01); *A61K 31/192* (2013.01); *A61K 31/4402* (2013.01); *A61K 31/485* (2013.01); *A61K 47/08* (2013.01);
(Continued)

(58) Field of Classification Search
CPC ................ A61K 31/137; A61K 31/167; A61K 31/4402; A61K 31/485; A61K 47/08; A61K 47/10; A61K 47/26; A61K 47/36; A61K 9/0095; A61K 9/08; Y10T 436/173845
See application file for complete search history.

(56) References Cited

U.S. PATENT DOCUMENTS 5,154,926 A  10/1992  Kawasaki et al.
5,422,100 A  6/1995  Eliaz et al.
(Continued)

FOREIGN PATENT DOCUMENTS

WO  WO20070089652  8/2007
WO  WO2007122581 A2  11/2007
(Continued)

OTHER PUBLICATIONS

12733M International Search Report dated Jun. 16, 2014.
(Continued)

*Primary Examiner* — Savitha M Rao
(74) *Attorney, Agent, or Firm* — Amanda Herman

(57) ABSTRACT

An anise flavored liquid medication. The liquid medication contains phenylephrine and an anethole analog that is substantially free of aldehyde groups. In one example, the anethole analog can be 1-methoxy-4-n-propylbenzene.

16 Claims, 3 Drawing Sheets

Related U.S. Application Data continuation of application No. 14/179,606, filed on Feb. 13, 2014, now Pat. No. 9,457,085.

(60) Provisional application No. 61/764,002, filed on Feb. 13, 2013.

(51) Int. Cl.

| | |
|---|---|
| *A61K 31/167* | (2006.01) |
| *A61K 31/4402* | (2006.01) |
| *A61K 31/485* | (2006.01) |
| *A61K 9/00* | (2006.01) |
| *A61K 9/08* | (2006.01) |
| *A61K 31/138* | (2006.01) |
| *A61K 31/192* | (2006.01) |
| *A61K 47/10* | (2017.01) |
| *A61K 47/26* | (2006.01) |
| *A61K 47/36* | (2006.01) |

(52) U.S. Cl.
CPC ............. *A61K 47/10* (2013.01); *A61K 47/26* (2013.01); *A61K 47/36* (2013.01); *Y10T 436/173845* (2015.01)

(56) References Cited

U.S. PATENT DOCUMENTS

| | | | |
|---|---|---|---|
| 5,458,879 | A | 10/1995 | Nikhilesh et al. |
| 6,599,883 | B1 | 7/2003 | Romeo et al. |
| 6,699,502 | B1 | 3/2004 | Fanara et al. |
| 7,414,152 | B2 | 8/2008 | Galopin et al. |
| 7,544,348 | B2 | 6/2009 | Jacob et al. |
| 7,547,433 | B2 | 6/2009 | Jacob et al. |
| 9,078,824 | B2 | 7/2015 | Cimiluca et al. |
| 9,194,429 | B2 | 11/2015 | Ashmore et al. |
| 9,457,085 | B2 | 10/2016 | Kaufmann et al. |
| 2006/0188450 | A1 | 8/2006 | Clarot |
| 2007/0148283 | A1 | 6/2007 | Harvey et al. |
| 2007/0249566 | A1 | 10/2007 | Martin et al. |
| 2007/0249727 | A1 | 10/2007 | Martin et al. |
| 2008/0008667 | A1 | 1/2008 | Hoke et al. |
| 2008/0014267 | A1 | 1/2008 | Giordano et al. |
| 2008/0026055 | A1 | 1/2008 | Fubara et al. |
| 2008/0300314 | A1 | 12/2008 | Galopin et al. |
| 2009/0155189 | A1 | 6/2009 | Kovacs et al. |
| 2009/0280160 | A1 | 11/2009 | Monteith et al. |
| 2010/0086498 | A1 | 4/2010 | Haught et al. |
| 2010/0278991 | A1 | 11/2010 | Haught et al. |
| 2016/0361277 | A1 | 12/2016 | Kaufmann et al. |

FOREIGN PATENT DOCUMENTS

| | | |
|---|---|---|
| WO | WO2010019730 A1 | 2/2010 |
| WO | WO2010128026 A2 | 11/2010 |

OTHER PUBLICATIONS

Buhse, Lucinda et al., "Topical drug classification", International Journal of Pharmaceutics, 295, 2005, pp. 101-112.

Cepacol Dual Relief Spray, www.Cepacol.com/products/spray.asp, Jan. 2009.

Khandwala, Atul et al., "5% Amlexanox oral paste, a new treatment for recurrent minor aphthous ulcers", Oral Surgery Oral Medicine Oral Pathology, vol. 83, No. 2, Feb. 1997, pp. 222-230.

Zicam Cough & Mist 8 hour max formula, www.Zicam.com/products/coughmax_spray, May 21, 2009.

All Office Actions, U.S. Appl. No. 13/021,903, filed Feb. 7, 2011.
All Office Actions, U.S. Appl. No. 12/274,705, filed Nov. 20, 2008.
All Office Actions, U.S. Appl. No. 14/179,606, filed Feb. 13, 2014.
All Office Actions, U.S. Appl. No. 15/247,955, filed Aug. 26, 2016.

anethole 1-methoxy-4-n-propylbenzene (MPB)

ANISE FLAVORED MEDICATION

FIELD OF THE INVENTION

The present invention is directed towards medication, more particularly anise flavored liquid medication that comprises phenylephrine hydrochloride.

BACKGROUND OF THE INVENTION

Flavors are commonly added to liquid medications to mask the unpleasant taste that many actives have. Anise flavoring has been widely used in liquid medications, in particular nighttime multi-symptom relief (MSR) cold/flu medications. Many consumers enjoy, trust, and expect this flavor.

Some consumers would like an anise flavored MSR cold/flu medication that also contains phenylephrine hydrochloride (PE), a decongestant. However, this formulation is not currently sold because it has surprisingly been found that anise flavoring comprising trans-anethole causes PE to degrade, which makes the liquid medication less effective and significantly reduces the shelf life of the product.

Therefore, there is a need for an anise flavored liquid medication that comprises PE and where the composition has a shelf life of at least 18 months.

SUMMARY OF THE INVENTION

An anise flavored liquid medication comprising: (a) phenylephrine; and (b) an anethole analog that is substantially free of aldehyde groups.

A dose of an anise flavored liquid medication comprising: (a) 650 mg acetaminophen; (b) 20 mg dextromethorphan; (c) 12.5 mg doxylamine succinate; (d) 10 mg phenylephrine hydrochloride; and (e) an anethole analog.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Flavoring is frequently added to liquid medications to mask the unpleasant taste of some actives. Anise flavoring has been widely used in liquid medications.

Currently, anise flavoring cannot be formulated with PE because the PE degrades. The inventors surprisingly found that trans-anethole, which is commonly found in anise flavoring, causes PE to degrade. Therefore, it was necessary to find a compound that tastes similar to anise that does not cause PE degradation. Furthermore, the PE stability must be balanced with a formulation with the desired taste and if present, the stability of other actives.

Figure 1:
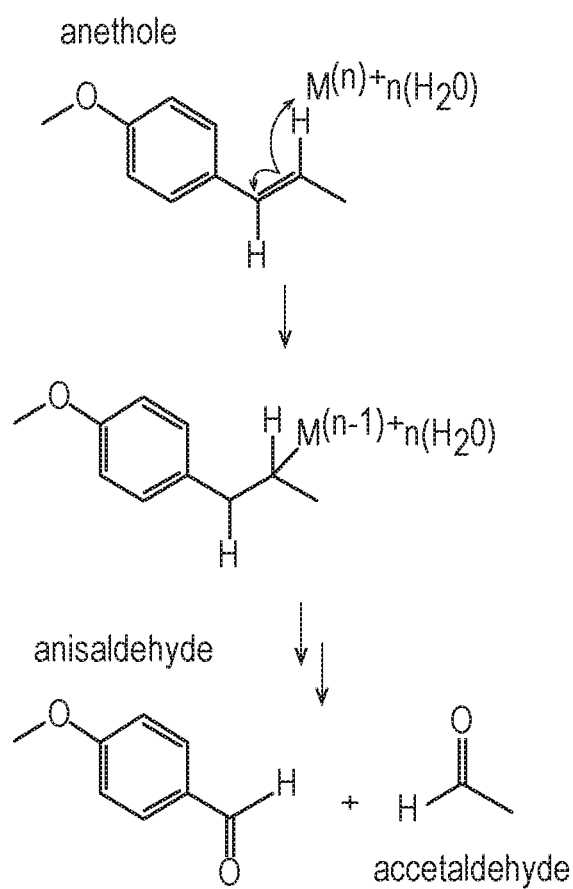
FIG. 1 shows a proposed mechanism for trans-anethole to degrade to form two aldehydes.

It is known that aldehydes, which are frequently found in flavoring, in particular cherry flavoring, cause PE degradation in liquid medications. Phenylephrine degradation in the presence of aldehydes is described in U.S. patent application Ser. No. 11/408,299. However, it was surprisingly found that formulations comprising trans-anethole showed accelerated degradation of phenylephrine. While not wishing to be bound by theory, it is believed that the trans-anethole degrades to form two PE-reactive aldehydes, anisaldehyde and acetaldehyde, as illustrated in FIG. 1.

Since trans-anethole causes PE loss in liquid medication, it was necessary to find a compound that has similar properties to trans-anethole, in particular a similar aroma and taste profile, but does not cause PE to degrade over time. The compound also needed to provide a shelf life of at least eighteen months. It was surprisingly found that an analog of trans-anethole that is substantially free of aldehyde groups can have a similar taste and aroma profile and give the desired shelf life. This was surprising because although the analog is chemically similar to trans-anethole, structural analogs are not necessarily functional analogs and can frequently have very different physical, chemical, biochemical, or pharmacological properties.

Non-limiting examples of anethole analogs can include 1-methoxy-4-n-propylbenzene, methyl anisate, anisole, 2-chloroanethole, 2,6-dichloroanethole, 3-nitroanethole, 3,5-dinitroanethole, 3-cyanoanethole, 3,5-dicyanoanethole, 1-methoxy-3-(1-propenyl)benzene, and combinations thereof.

In one example, the anethole analog is 1-methoxy-4-n-propylbenzene (dihydroanethole). When the concentration of dihydroanethole was adjusted to take into account the analog's unique properties, such as its propensity to have a lower aroma and taste threshold, and, a less sweet, drier, almost woody aftertaste than trans-anethole, it was surprisingly found that dihydroanethole was an acceptable substitute for trans-anethole. In one example, additional flavor ingredients can be added to modify the overall sensory experience as desired.

Figure 2A:
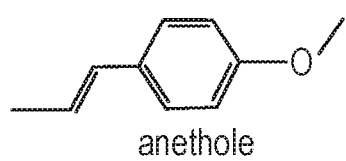
FIG. 2A shows the chemical structure of trans-anethole (CAS #104-45-0)
Figure 2B:
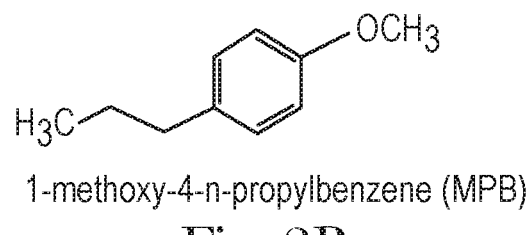
FIG. 2B shows the chemical structure of 1-methoxy-4-n-propylbenzene.

FIG. 2 compares the structures of FIG. 2A, trans-anethole, and FIG. 2B, the anethole analog dihydroanethole. Trans-anethole has a carbon chain with a double bond, which is the proposed source of aldehyde formation via the mechanism in FIG. 1. However, dihydroanethole does does not have this double bond and therefore does not break down to form aldehydes.

The present invention uses an anethole analog in the formulation of a medicament that comprises PE and tastes like anise.

As used herein, "dose" refers to a volume of liquid medication containing an amount of a drug active suitable for administration on a single occasion, according to sound medical practice. A dose can be orally administered and is typically swallowed immediately. In one example, a dose can be about 30 mL, in another example about 25 mL, in another example about 20 mL, in another example about 15 mL, and in another example about 10 mL. The concentration of active ingredients can be adjusted to provide the proper doses of actives given the liquid dose size As used herein, "medication" refers to medications, such as pharmaceuticals, including prescription medications and/or over-the-counter medications. In some examples, a medication can be a supplement.

As used herein, "shelf life" refers to the length of time a liquid medication is given following manufacture before it is considered unsuitable for sale or consumption. A liquid medication comprising PE is considered unsuitable for sale when the PE concentration is 10% lower than the level claimed on the label. In one example, the shelf life is greater than about 6 months, in another example greater than about 12 months, in another example greater than about 18 months, and another example greater than about 24 months, in another example greater than about 30 months, and in another example greater than about 36 months. Shelf life can be determined by performing the Accelerated Stability Test Method, described hereafter. If no significant change in concentration of the actives is found during the three-month period of the Acceleratred Stability Test, then the product can be typically placed in the market with a shelf-life of up to two years. For a pharmaceutical product a "significant change" is defined by the International Conference on Harmonization (ICH) as a 5% change in concentration from its initial value at t=0.

Since consumers generally suffer from a few colds per year, it is important that the cold products have a shelf life that allows them to used for multiple colds. When consumers are feeling sick, they do not want to purchase more products because theirs has expired. Furthermore, a longer shelf life gives the store more time to sell the product. Some stores will not sell a pharmaceutical product where the product will expire within twelve months, since that is not acceptable to consumers. Therefore, products that have greater stability are more advantageous.

In one example, the mean loss of PE concentration is less than about 6.5% within a 95% confidence interval over 6 months according to the Accelerated Stability Test Method, described hereafter, in another example less than about 6% within a 95% confidence interval, in another example less than about 5.5% within a 95% confidence interval, in another example less than about 5% within a 95% confidence interval, in another example about 4.5% within a 95% confidence interval, in another example less than about 4% within a 95% confidence interval, and in another example less than about 3.5% within a 95% confidence interval.

Figure 3:
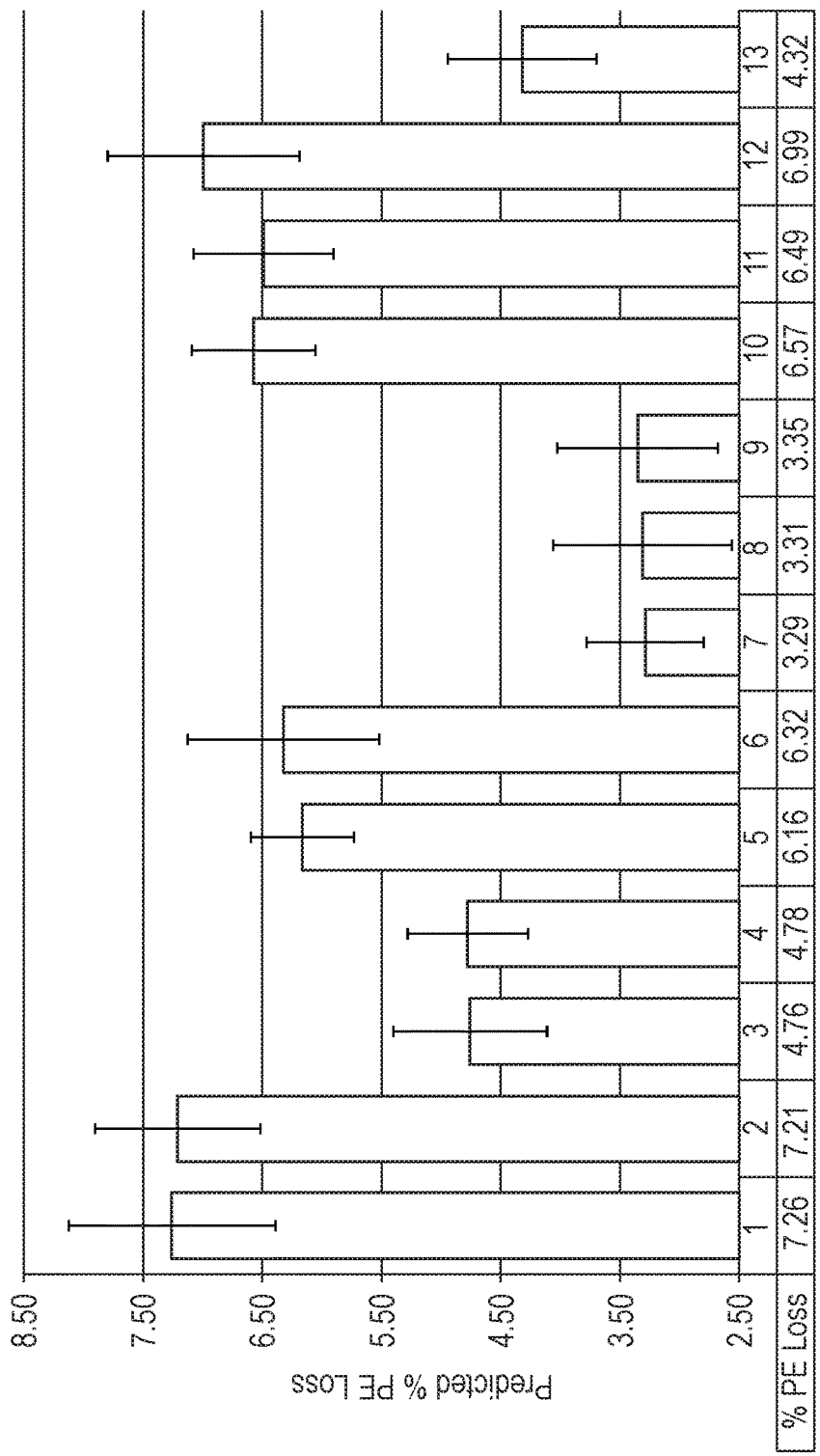
FIG. 3 shows the predicted percentage of PE loss after six months at 40° C., of thirteen different examples, as determined by the AFRICA Stability Test Method.

FIG. 3 shows the predicted percentage of PE loss after six months at 40° C., 75% relative humidity. The twelve examples that were tested in FIG. 1 were tested using the AFRICA Stability Test Method, described hereafter. The twelve examples correspond to Examples 1-12, described hereafter. Examples 7, 8, and 9 have the best PE stability and these formulations could be used in compositions that have a shelf life of at least two years.

FIG. 3 shows that that Example 1, a formulation comprising anise flavoring, which comprises many flavoring components including trans-anethole, and Example 2, a formulation comprising trans-anethole and no other flavoring components, have the most PE degradation. Furthermore, the PE degradation for both Example 1 and 2 is statistically the same. This observation led the inventors to determine that trans-anethole was primarily responsible for the PE degradation. The PE loss that was observed in Examples 1 and 2 is too high and the shelf life would be significantly shorter than 24 months.

Example 3, which had no flavoring component, was tested and it had significantly less PE degradation than Examples 1 and 2. This observation further confirmed that a significant amount of PE degradation is from the anise flavoring, in particular the trans-anethole.

Examples 4, 5, and 6 all had varying amounts of the anethole analog dihydroanethole. Example 4 had the least amount of PE loss and between Examples 4, 5, and 6, and is the most commercially desirable from a stability perspective. However, Examples 4, 5, and 6 are not the most desirable from a taste perspective, since dihydroanethole has a stronger taste than trans-anethole.

Examples 7, 8, and 9 all have 0.00025% (2.5 ppm) dihydroanethole and varying amounts of xanthan gum. Xanthan gum is a thickener and therefore compositions that comprise more xanthan gum will have a greater viscosity. It has been found that 0.00025% (2.5 ppm) dihydroanethole can provide the desired level of anise flavor. There is no statistical difference between the stability in Examples 7, 8, and 9 and therefore, the amount of xanthan gum in the composition did not impact the stability of the PE. All three examples have less than 5% PE loss and could be marketed with a shelf life of at least about two years.

Examples 10, 11, and 12 have varying amounts of anise flavoring comprising trans-anethole. These examples show that even Example 10, which has 25% of the anise flavoring with trans-anethole of Example 1, can cause significant PE loss. The PE loss that was observed in Examples 10, 11, and 12 is too high and the shelf life would be significantly shorter than 24 months.

Examples 13 and 14 compare two formulas, one without ethanol (Example 13) and another with 7.25% of 95% ethanol (Example 14). Ethanol can provide superior sensory benefits and can also help with the solubility of the anethole analog, as well as other flavoring components, and actives in the solution. Ethanol can also be desirable in a liquid medication that is intended for nighttime use. In one example, the composition comprises 3% to 15% ethanol, in another example 4% to 12% ethanol, in another example 5% to 9% ethanol, and in another example 6% to 8% ethanol.

The stability of PE must also be balanced with a consumer acceptable taste. Some consumers prefer a composition that has a subtle impression of anise flavor. Some consumers also prefer a slightly medicinal taste. It has been found that it is difficult for consumers to notice the anise flavor if it is too low. However, if the dihydroanethole is too high, consumers complain that the formulation tastes too medicinal and some consumers complain that the formulation tastes like diesel fuel. In another example, the liquid medication comprises from about 1 ppm to about 50 ppm anethole analog, in another example from about 1 ppm to about 40 ppm anethole analog, in another example from about 1 ppm to about 30 ppm anethole analog, in another example from about 1 ppm to about 20 ppm anethole analog, in another example from about 1 ppm to about 10 ppm anethole analog, and in another example from about 1 ppm to about 5 ppm anethole analog. In one example, the liquid medication has from about 1 ppm to about 10 ppm dihydroanethole, in another example from about 1.5 ppm to about 7 ppm dihydroanethole, and in another example about 2 ppm to about 5 ppm dihydroanethole. In one example, the liquid medication comprises about 3 ppm dihydroanethole. Less dihydroanethole can be used than anise flavoring that contains trans-anethole because dihydroanethole has a stronger flavor than trans-anethole.

In one example, the liquid pharmaceutical composition comprises no trans-anethole, in another example the composition comprises less than about 0.001% trans-anethole, in another example the composition comprises less than about 0.01% trans-anethole, and in another example the composition comprises less than about 0.025% trans-anethole.

pH can also impact the stability of the liquid medication. A lower pH can increase the amount of APAP that degrades as the medication ages. When APAP ages, it not only becomes less effective, it also makes the solution slightly brown, which is not acceptable to consumers.

However, PE is more stable at a lower pH. Therefore, the pH must be balanced so APAP and PE are both stable. In one example, the liquid medication has a pH of about 2 to about 6, in another example from about 3 to about 5.75, in another example from about 3.5 to about 5.5, in another example from about 3.75 to about 5.25, and in another example from about 4 to about 5.

In one example, the liquid medication can comprise from 0.005% to 0.5% PE, in another example 0.01% to 0.1% PE, and in another example 0.02% to 0.04% PE. In one example the liquid medication can comprise 5 mg PE per dose, in another example 10 mg PE per dose, and in another example 20 mg PE per dose.

A dose of liquid medication can be from about 10 mL to about 75 mL, in another example from about 15 mL to about 50 mL, in another example from about 25 mL to about 40 mL, and in another example from about 28 mL to about 35 mL. In one example, a dose of the liquid medication is about 30 mL, in another example about 20 mL, and in another example about 15 mL. In one example, the dose is intended to be administered every 4 hours, in another example every 6 hours, in another example every 8 hours, and in another example every 12 hours.

In addition to comprising PE, the liquid compositions can comprise one or more drug actives in addition to PE. In one example, the drug actives can be immediate release drug actives, extended release drug actives, or delayed release drug actives. In one example, the additional drug active can be formulated as particles and in another example the active can be formulated as coated beads.

In one example, the additional drug active is a MSR cold/flu active which can be used to treat one or more cold/flu symptoms. MSR cold/flu actives can be used to treat a variety of cold/flu symptoms including nasal congestion, runny nose, sneezing, headache, dry cough, sore throat, sinus pressure or pain, chest congestion, muscle aches/pains, wet/chesty cough, fever, and combinations thereof. MSR cold/flu actives can include decongestants, expectorants, antihistamines, antitussives, pain relievers, and combinations thereof.

In one example, MSR cold/flu actives can be formulated for daytime use or nighttime use. In one example, the liquid medication comprises instructions that direct a user to ingest the medication at night before bedtime.

Non-limiting examples of expectorants can include guaifenesin, ambroxol, bromhexine, and combinations thereof. In one example, the expectorant can be guaifenesin. In one example a dose can comprise 200 mg of guaifenesin and in another example 400 mg of guaifenesin.

Non-limiting examples of antihistamines can include chlorpheniramine, desloratadine, levocetirizine, diphenhydramine, doxylamine succinate, triprolidine, clemastine, pheniramine, brompheniramine, dexbrompheniramine, loratadine, cetirizine and fexofenadine, amlexanox, alkylamine derivatives, cromolyn, acrivastine, ibudilast, bamipine, ketotifen, nedocromil, omalizumab, dimethindene, oxatomide, pemirolast, pyrrobutamine, pentigetide, thenaldine, picumast, tolpropamine, ramatroban, repirinast, suplatast tosylate aminoalkylethers, tazanolast, bromodiphenhydramine, tranilast, carbinoxamine, traxanox, chlorphenoxamine, diphenylpyaline, embramine, p-methyldiphenhydramine, moxastine, orphenadrine, phenyltoloxamine, setastine, ethylenediamine derivatives, chloropyramine, chlorothen, methapyrilene, pyrilamine, talastine, thenyldiamine, thonzylamine hydrochloride, tripelennamine, piperazines, chlorcyclizine, clocinizine, homochlorcyclizine, hydroxyzine, tricyclics, phenothiazines, mequitazine, promethazine, thiazinamium methylsulfate, azatadine, cyproheptadine, deptropine, desloratadine, isothipendyl, olopatadine, rupatadine, antazoline, astemizole, azelastine, bepotastine, clemizole, ebastine, emedastine, epinastine, levocabastine, mebhydroline, mizolastine, phenindamine, terfenadine, tritoqualine, and combinations thereof.

In one example the liquid composition can comprise from about 0.01% to about 0.1% antihistamine, in another example from about 0.02% to about 0.07% antihistamine, and in another example from about 0.03% to about 0.05% antihistamine In one example, the antihistamine can be doxylamine succinate and a dose of liquid medication can comprise 12.5 mg doxylamine succinate. In another example, the antihistamine can be chlorpheniramine In one example a dose can comprise 2 mg of chlorpheniramine and in another example a dose can comprise 4 mg of chlorpheniramine Non-limiting examples of antitussives can include dextromethorphan HBr (DXM), codeine, chlophedianol, levodropropizine, and combinations thereof. In one example the liquid medication can comprise from about 0.01% to about 0.2% antitussive, in another example from about 0.025% to about 0.1%, and in another example from about 0.04% to about 0.075% antitussive. In one example the antitussive can be selected from the group consisting of DXM, chlophedianol, and combinations thereof. In one example a dose can comprise 15 mg DXM, in another example 20 mg DXM, and in another example 30 mg DXM. In another example a dose can comprise 12.5 mg chlophedianol.

Non-limiting examples of pain relievers can include APAP, ibuprofen, ketoprofen, diclofenac, naproxen, aspirin, and combinations thereof. In one example the liquid medication can comprise from about 0.5% to about 3.5% pain reliever, in another example from about 1% to about 3% pain reliever, and in another example from about 1.5% to about 2% pain reliever. In one example the pain relievers can include APAP, ibuprofen, naproxen, or combinations thereof. In one example a dose can comprise 325 mg to 500 mg APAP, in another example 200 mg ibuprofen, and in another example, 200 mg naproxen.

In one example, the cold/flu dosage unit can further comprise a stimulant such as caffeine.

In one example, the dosage units can comprise one or more MSR cold/flu actives, in another example two or more MSR cold/flu actives, in another example three or more MSR cold/flu actives, and in another example four or more MSR cold/flu actives. In one example, the dosage unit can comprise exactly one MSR cold/flu active, in another example exactly two MSR cold/flu actives, in another example exactly three MSR cold/flu actives, and in another example exactly four MSR cold/flu actives. In one example the dosage units can comprise APAP, doxylamine succinate, DXM, and PE.

The compositions can comprise a sweetener to provide sweetness and taste masking of the PE as well as any additional actives that may be present. In one example, the composition comprises from about 2% to 25% sweetener, in another example from about 5% to 20% sweetener, in another example from about 7% to 15% sweetener, and in another example from about 8% to 12% sweetener. Non-limiting examples of sweeteners can include nutritive sweeteners, sugar alcohols, synthetic sugars, high intensity natural sweeteners, and combinations thereof.

Non-limiting examples of nutritive sweeteners can include fructose, galactose, and combinations thereof.

In one example, the liquid composition does not comprise glucose because glucose is an aldehyde. In another example, the liquid composition does not comprise sucrose, including liquid sucrose, because sucrose can hydrolyze to its constituent sugars, namely glucose and fructose. In another example, the liquid compositions do not comprise high fructose corn syrup.

Non-limiting examples of sugar alcohols can include xylitol, sorbitol, mannitol, maltitol, lactitol, isomalt, erthritol, glycerin, and combinations thereof. In one example the composition can comprise from about 1% to about 30% sugar alcohol, in another example from about 5% to about 28% sugar alcohol, in another example about 10% to about 25% sugar alcohol, and in another example about 15% to about 23% sugar alcohol. In one example the composition comprises from about 5% to about 20% sorbitol, in another example from about 7% to about 18% sorbitol, and in another example from about 10% to about 15% sorbitol. In another example, the composition comprises from about 3% to about 15% glycerin, in another example from about 5% to about 10% glycerin, and in another example from about 7% to about 9% glycerin.

Non-limiting examples of synthetic sweeteners can include sodium saccharin, acesulfame potassium, sucralose, aspartame, monoammonium glycyrrhizinate, neohesperidin dihydrochalcone, thaumatin, neotame, cyclamates, and mixtures thereof. In one example the composition can comprise from about 0.01% to about 0.5% artificial sweetener, in another example from about 0.1% to about 0.3% artificial sweetener, and in another example about 0.15% to about 0.25% artificial sweetener.

Non-limiting examples of high intensity natural sweeteners can include neohesperidin dihydrochalcone, stevioside, rebaudioside A, rebaudioside C, dulcoside, monoammonium glycrrhizinate, thaumatin, and combinations thereof.

The present liquid components typically comprise a solvent. A solvent can be used to dissolve the anethole analog, phenylephrine and/or other active(s) into solution.

Non-limiting examples of solvents can include water, propylene glycol, ethanol, and mixtures thereof. In one example the composition comprises from about 60% to about 95% solvent, in another example from about 70% to about 90% solvent, and in another example from about 80% to about 88% solvent.

In one example, the composition comprises water and propylene glycol. In one example, the composition comprises from about 35% to about 75% water, in another example from about 40% to about 65% water, in another example from about 45% to about 60% water, and in another example from about 48% to about 56% water. In another example, the composition can comprise from about 10% to about 35% propylene glycol, in another example from about 15% to about 30% propylene glycol, and in another example from about 20% to about 25% propylene glycol.

In one example, the composition comprises a buffer. The buffer can help maintain a constant pH within the liquid composition. In one example the liquid composition comprises from about 0.05% to about 2% buffer, in another example from about 0.1% to about 1% buffer, in another example from about 0.15% to about 0.5% buffer, and in another example from about 0.18% to about 0.25% buffer. Buffers can include acetate buffers, citrate buffers, and phosphate buffers. Non-limiting examples of buffers can include acetic acid, sodium acetate, citric acid, sodium citrate, monobasic sodium phosphate, dibasic sodium phosphate, sodium carbonate, sodium bicarbonate, succinic acid, sodium succinate, potassium dihydrogen phosphate, and phosphoric acid.

In one example, the composition comprises a preservative. In one example the liquid composition comprises from about 0.01% to about 1% preservative, in another example from about 0.05% to about 0.5% preservative, in another example from about 0.07% to about 0.3% preservative, and in another example from about 0.08% to about 0.15% preservative. Non-limiting examples of preservatives can include benzalkonium chloride, ethylenediaminetetraacetic acid (EDTA), benzyl alcohol, potassium sorbate, parabens, benzoic acid, sodium benzoate, and mixtures thereof.

In one example, the composition comprises a thickener. In one example the liquid composition comprises from 0.01% to 3% thickener, in another example 0.05% to 1.5% thickener, in another example 0.1% to 0.75% thickener, and in another example 0.12% to 0.3% thickener. Non-limiting examples of thickeners can include xanthan gum, carrageenan, polyacrylic acid, polyvinylpyrrolidone, cellulosic polymers including carboxymethycellulose, hydroxethylcellulose, hydroxymethylcellulose, and hydroxypropylmethylcellulose, and combinations thereof.

The liquid composition can optionally include one or more sensates. Non-limiting examples of sensates can include cooling sensates, warming sensates, tingling sensates, and combinations thereof. Sensates can useful to deliver signals to the user.

Non-limiting examples of cooling sensates can include WS-23 (2-Isopropyl-N,2,3-trimethylbutyramide), WS-3 (N-Ethyl-p-menthane-3-carboxamide), WS-30 (1-glyceryl-p-mentane-3-carboxylate), WS-4 (ethyleneglycol-p-methane-3-carboxylate), WS-14 (N-t-butyl-p-menthane-3-carboxamide), WS-12 (N-(4-,ethoxyphenyl)-p-menthane-3-carboxamide), WS-5 (Ethyl-3-(p-menthane-3-carboxamido) acetate, Menthone glycerol ketal (sold as Frescolat® MGA by Haarmann & Reimer), (−)-Menthyl lactate (sold as Frescolat® ML by Haarmann & Reimer), (−)-Menthoxypropane-1,2-diol(sold as Coolant Agent 10 by Takasago International), 3-(1-menthoxy)propane-1,2-diol, 3-(1-Menthoxy)-2-methylpropane-1,2-diol, (−)-Isopulegol is sold under the name "Coolact P®" by Takasago International., cis & trans p-Menthane-3,8-diols(PMD38)—Takasago International, Questice® (menthyl pyrrolidone carboxylate), (1R,3R,4S)-3-menthyl-3,6-dioxaheptanoate—Firmenich, (1R,2S,5R)-3-menthyl methoxyacetate—Firmenich, (1R,2S,5R)-3-menthyl 3,6,9-trioxadecanoate—Firmenich, (1R,2S,5R)-menthyl 11-hydroxy-3,6,9-trioxaundecanoate—Firmenich, (1R,2S,5R)-3-menthyl (2-hydroxyethoxy)acetate—Firmenich, Cubebol—Firmenich, Icilin also known as AG-3-5, chemical name 1-[2-hydroxyphenyl]-4-[2-nitrophenyl-1-1,2,3,6-tetrahydropyrimidine-2-one), 4-methyl-3-(1-pyrrolidinyl)-2[5H]-furanone, Frescolat ML—menthyl lactate, Frescolat MGA—menthone glycerin acetal, Peppermint oil, L-Monomenthyl succinate, L-monomenthyl glutarate, 3-1-menthoxypropane-1,2-diol—(Coolact 10), 2-1-menthoxyethanol (Cooltact 5), TK10 Coolact (3-1-Menthoxy propane-1,2-diol), Evercool™ 180 (N-(4-cyanomethylphenyl)-p-menthanecarboxamide)), and combinations thereof. In one example, the composition can comprise from about 0.005% to about 1% cooling sensate, in another example from about 0.05% to about 0.5% cooling sensate, and in another example from about 0.01% to about 0.25% cooling sensate.

In one example, the cooling sensate can be EverCool™ 180 (available from Givaudan of Cincinnati, Ohio, as a 5% solution of N-(4-cyanomethylphenyl)-p-menthanecarboxamide in a flavoring ingredient cool white grape, or as a 7.5% solution of N-(4-cyanomethylphenyl)-p-menthanecarboxamide in a flavor ingredient such as spearmint or peppermint.

Non-limiting examples of warming sensates can include TK 1000, TK 1 MM, Heatenol—Sensient Flavors, Optaheat—Symrise Flavors, Cinnamon, Capsicum, Capsaicin, Curry, FSI Flavors, Isobutavan, Nonivamide 60162807, Hotact VEE, Hotact 1MM, piperine, optaheat 295 832, optaheat 204 656, optaheat 200 349, and combinations thereof. Warming sensates can be present from about 0.005% to about 2%, in another example from about 0.01% to about 1%, and in another example from about 0.1% to about 0.5%.

Non-limiting examples of tingling sensates can include sichuan pepper, hydroxy alpha sanshool, Jambu extracts, spilanthol, and combinations thereof. In one example, tingling sensates can be present from about 0.005% to about 1%, in another example from about 0.01% to about 0.5%, and another example from about 0.015% to about 0.3%.

In addition to comprising an anethole analog, the composition can comprise additional flavoring ingredients. In one example, the flavoring ingredient does not comprise an aldehyde. When present, flavoring ingredients are generally used in the compositions at levels of from about 0.001% to about 8%, by weight of the composition.

Additional non-limiting examples of flavoring ingredients can include peppermint oil, corn mint oil, spearmint oil, oil of wintergreen, clove bud oil, cassia, sage, parsley oil, marjoram, lemon, lime, orange, mango, cis-jasmone, 2,5-dimethyl-4-hydroxy-3(2H)-furanone, 5-ethyl-3-hydroxy-4-methyl-2(5H)-furanone, vanillin, ethyl vanillin, propenyl guaethol, heliotropine, 4-cis-heptenal, diacetyl, methyl-p-tert-butyl phenyl acetate, menthol, methyl salicylate, ethyl salicylate, 1-menthyl acetate, oxanone, alpha-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, alpha-terpineol, linalool, limonene, citral, maltol, ethyl maltol, carvone, menthone, β-damascenone, ionone, gamma decalactone, gamma nonalactone, gamma undecalactone and mixtures thereof. Generally suitable flavoring ingredients are those containing structural features and functional groups that are less prone to redox reactions. These include derivatives of flavouring ingredients that are saturated or contain stable aromatic rings or ester groups. In one example, the composition comprises from about 0.01% to about 1% flavoring ingredients, in another example from about 0.05% to about 0.5% flavoring ingredients, and in another example from about 0.1% to about 0.3% flavoring ingredients.

The composition can optionally include one or more salivation agents. Non-limiting examples of salivation agents include formula (I):

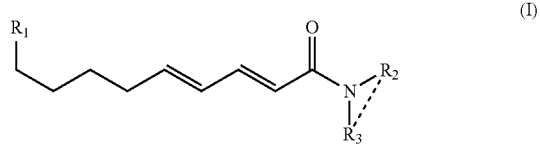

(I)

wherein $R_1$ represents C1-C2 n-alkyl; $R_2$ is 2-methyl-1-propyl and $R_3$ is hydrogen, or $R_2$ and $R_3$ taken together is a moiety (designated by the dashed lines) having the formula —$(CH_2)_n$— wherein n is 4 or 5, and combinations thereof.

In an embodiment, the salivating agent comprises a material wherein $R_2$ is 2-methyl-1-propyl and $R_3$ is hydrogen, in another embodiment the salivating agent comprises a material wherein $R_1$ is C1 n-alkyl, $R_2$ is 2-methyl-1-propyl and $R_3$ is hydrogen. In another embodiment, the salivating agent comprises trans-pellitorin, a chemical having a structure according to formula (II):

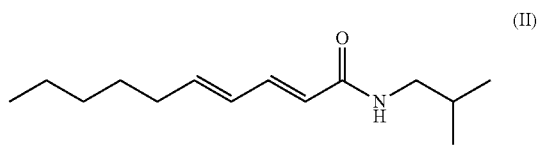 [SMILES: CCCCC/C=C/C=C/C(=O)NCC(C)C]

(II)

In another embodiment, the salivation agent can include sodium bicarbonate, sodium chloride, trans-pellitorin, and combinations thereof. In one example, salivation agents can be present from about 0.05% to about 2%, in another embodiment from about 0.1% to about 1%, and in another example from about 0.25%% to about 0.75%.

The liquid composition can be any color. Non-limiting examples of colors can include red, green, amber, orange, yellow, blue, pink, violet, turquoise, and combinations thereof. In one example, the composition is green. In another example, the liquid composition is clear.

The composition can also comprise a dye that provides the color. Non-limiting examples dyes that may be used in the present invention include FD&C blue #1, FD&C blue #2, D&C blue #4, D&C blue #9, FD&C green #3, D&C green #5, D&C green #6, D&C green #8, D&C orange #4, D&C orange #5, D&C orange #10, D&C orange #11, FD&C red #3, FD&C red #4, D&C red #6, D&C red #7, D&C red #17, D&C red #21, D&C red #22, D&C red #27, D&C red #28, D&C red #30, D&C red #31, D&C red #33, D&C red #34, D&C red #36, D&C red #39, FD&C red #40, D&C violet #2, FD&C yellow #5, FD&C yellow #6, D&C yellow #7, Ext. D&C yellow #7, D&C yellow #8, D&C yellow #10, D&C yellow #11, and combinations thereof. In one example, the composition comprises from about 0.001% to about 0.1% dye, in another example from about 0.002% to about 0.05% dye, and in another example form about 0.003% to about 0.01% dye.

Accelerated Stability Test Method

Liquid medications containing PE are packaged in standard colorless polyethylene terephthalate (PET) bottles and placed in a controlled temperature chamber that is set to the ICH accelerated stability conditions of 40° C. and 75% relative humidity. At the following set time points: 0 days (t=0), 30 days, 60 days, 90 days, and six-months, a bottle is removed from the controlled temperature chamber Immediately after each bottle is removed, the Assay Method is performed to determine the % w/w PE in the liquid medication.

Assay Method

The Assay Method is used for the determination of % w/w PE in respiratory liquids. A Sample Preparation, as described below, is analyzed by reverse-phase High Performance Liquid Chromatography (HPLC) that uses a C18 column with trifluoroacetic acid (TFA) and acetonitrile (ACN) mobile phases and a single point external standard for quantification. Detection is by UV absorbance at 275 nm with detector response measured by peak area.

Sample Preparation (Results Reported in % w/w)

Tare an appropriate volumetric flask to provide the correct dilution to match the PE concentration of the prepared Working Standard, as described below. Transfer a sample of liquid medication into the volumetric flask and record the weight to the nearest 0.1 mg. Dilute the liquid medication in the volumetric flask and Q.S. to volume with water and mix thoroughly. Filter the liquid medication and the water with the aid of a disposable syringe and a syringe filter into an injection vial and cap, to form the Sample Preparation. Record the volume (mL) and weight (g) of the Sample Preparation for use in the calculation below.

Stock Standard Preparation

Depending on the concentration of the sample at t=0 and the weight of the Sample Preparation, Weigh an appropriate amount of PE reference standard obtained from the United States Pharmacopeia (USP) to the nearest 0.1 mg. The amount of PE reference standard depends on the PE concentration at t=0 and the weight of the Sample Preparation. Quantitatively transfer the PE reference standard to an appropriate volumetric flask. Next add Q.S. to volume with 0.1% v/v phosphoric acid solution. Mix until the PE reference standard has dissolved, to form the Stock Standard. Record the volume (mL) and the weight (g) of the Stock Standard. The PE concentration in the Stock Standard should be conducive for dilution to ensure the PE concentration of the Working Standard, as described below, is within the linear range of the UV detector at the specified wavelength found in Chromatographic Conditions.

Working Standard Solution Preparation

Dilute the Stock Standard so that it has the same PE concentration as the Theoretical Sample Preparation at t=0. The Theoretical Sample Preparation at t=0 is the target PE concentration of the sample at t=0, however, this may not be the actual concentration because the PE could start to degrade instantaneously upon manufacturing and therefore it is possible that the Theoretical Sample Preparation at t=0 could contain a higher PE concentration than the Sample Preparation at t=0.

Pipette an appropriate volume of Stock Standard into an appropriate volumetric flask. Add 0.1% v/v phosphoric acid to volume and mix thoroughly to form the Working Standard. Record the volume (mL) and the dilution factor for the Working Standard. The final concentration of PE in the Working Standard should be in the linear range of the UV detector at the specified wavelength found in the chromatographic conditions.

Mobile Phase Preparation

Next, prepare the aqueous and organic mobile phase components, Mobile Phase A and B, respectively. To prepare Mobile Phase A, add 1 mL of TFA per 1 L of purified water. For Mobile Phase B, use 100% ACN. Mobile Phase A and B will be used to perform the reverse-phase gradient chromatography as described in USP Chapter <621> and the Chromatographic Conditions described below.

Chromatographic Conditions

The Waters XBridge™ reverse-phase HPLC columns (available from Waters Corporation, Milford, Mass.) are equipped with a 4.6×150 mm column that contains a 3.5 μm C18 packing material. The column temperature is 40° C. with the flow rate at 1.0 mL/min and the detector wavelength is 275 nm. The sample injection volume is 10 μL. Certain conditions such as the column temperature, flow rate, and mobile phase reagent ratio may be altered or changed provided that adequate resolution and sensitivity are obtained per USP Chapter <621> and system suitability criteria, as described below, are met.

The following gradient elution program in addition to other parameters found in the Chromatography Conditions are used to analyze PE in both Working Standards and Sample Preparations:

| Time (mins) | % Mobile Phase A | % Mobile Phase B |
|---|---|---|
| 0.0 | 96 | 4 |
| 10.0 | 85 | 15 |
| 19.0 | 40 | 60 |
| 20.0 | 40 | 60 |
| 20.1 | 96 | 4 |
| 25.0 | 96 | 4 |

System Suitability

For system suitability, inject 10 μL of the Working Standard and chromatograph until system suitability is achieved with five successive injections. The system suitability is the % RSD (Relative Standard Deviation) for the peak areas and the retention times for PE.

If the liquid composition comprises APAP and DXM, the system suitability is the % RSD for the peak areas and the retention times for PE and Dextromethorphan HBr (DXM) should be 2.0% or less. Also the resolution between PE and DXM should be 2.0 or greater and the peak tailing for PE should be 2.5 or less. Peak retention order is PE followed by APAP, then DXM.

Next, inject 10 μL of the Sample Preparation and chromatograph and then inject 10 μL of the Working Standard, this is the bracket standard.

Then, inject 10 μL of the Sample Preparation and chromatograph. Repeat this step up with up to six samples before injecting 10 μL of the Working Standard.

Calculations $$\text{PE } (\% \text{ w/w}) = (W_S/V_{F1})*(P/100)*(DF)*(A_2/A_1)*(V_{F2}/WP)*(100)$$

Where $W_S$ in the weight of the Stock Standard (g), $V_{F1}$ is the volume of the Stock Standard (mL), P is the purity of the USP PE reference standard in % from the USP Certificate of Analysis, DF is the dilution factor of the Working Standard, $A_2$ is the chromatographic response of the Sample Preparation in peak area units, $A_1$ is the chromatographic response of the Working Standard in peak area units averaged from all Working Standards tested, which include system suitability and all bracket standards. $V_{F2}$ is the volume of the Sample Preparation and WP is the weight of the Sample Preparation. Chromatographic response of PE in peak area units is determined by integrating the PE peak with Empower 3 Chromatography Data Software (available from Waters, Corporation, Milford, Mass.).

Statistical Evaluation of PE Assay Data

A zero-order kinetic model is fit to the data using the % w/w PE values determined from the above calculation. This model can be used to determine the rate of PE loss and standard error associated with the dataset to yield 95% confidence intervals at the study endpoint of 6-months.

AFRICA Stability Test Method

The AFRICA Stability Test Method is performed the same as the Accelerated Stability Test Method described herein except the Stability Conditions and the Stability Predictions are different and are performed as described below.

Stability Conditions

Liquid medication samples containing PE were forcibly degraded in flow using an Automated Flow Reaction and Incubation Control Apparatus (AFRICA) (available from Syrris Inc., Charlestown, Mass.). This was accomplished using a temperature ramp ranging from 80° C. to 140° C. in 20° C. increments. In another example, the temperature range can be ramped in any suitable increments, for instance 10° C. increments, For each temperature, samples were stressed under pressure (6-7 bar) for 20 minutes prior to sampling for assay of PE.

Stability Prediction

Using % w/w PE values determined from HPLC assay of AFRICA samples, rates of loss (k) for each temperature were determined against % w/w PE values of an unexposed control sample. These losses were then converted into units suitable for an Arrhenius plot, where Arrhenius parameters were derived using standard linear regression. Percent predicted PE loss for each sample was accomplished using the calculated rate constant from the standard Arrhenius equation with accelerated stability conditions (40° C.) for temperature. The predicted % PE loss levels after 6-months of exposure are reported.

The AFRICA Stability Test Method can be used to determine the degradation of with any drug active, including but not limited to drug actives as described herein. In another example, the AFRICA Stability Test Method can be used to determine the degradation of oxymetazoline.

The temperature ramp can be any suitable temperature increment. In one example, the increment was accomplished using a temperature ramp ranging from 80° C. to 140° C. in 20° C. increments. In another example, the temperature range can be ramped in any suitable increments. Non-limiting examples of suitable ramp increments can include 5° C. increments, 10° C. increments, 15° C. increments, 20° C. increments, 25° C. increments, 30° C. increments, and combinations thereof.

EXAMPLES

The following example further describes and demonstrates embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., w/w percentages, unless otherwise specified.

The following compositions can be prepared in accordance with the present invention:

|  | 1 | 2 | 3 | 4 | 5 | 6 | 7 |
|---|---|---|---|---|---|---|---|
| Water | Q.S. | Q.S. | Q.S. | Q.S. | Q.S. | Q.S. | Q.S. |
| Propylene glycol | 23.02 | 23.02 | 23.02 | 23.02 | 23.02 | 23.02 | 23.02 |
| APAP | 2.00 | 2.00 | 2.00 | 2.00 | 2.00 | 2.00 | 2.00 |
| DXM | 0.062 | 0.062 | 0.062 | 0.062 | 0.062 | 0.062 | 0.062 |
| Doxylamine succinate | 0.038 | 0.038 | 0.038 | 0 | 0 | 0 | 0 |
| PE | 0.031 | 0.031 | 0.031 | 0.031 | 0.031 | 0.031 | 0.031 |
| Anise Flavoring with trans-Anethole | 0.21 | 0 | 0 | 0 | 0 | 0 | 0 |
| trans-Anethole | 0 | 0.013 | 0 | 0 | 0 | 0 | 0 |
| Dihydroanethole | 0 | 0 | 0 | 0.001 | 0.015 | 0.21 | 0.00025 |
| Xanthan gum | 0.15 | 0.15 | 0.15 | 0.15 | 0.15 | 0.15 | 0.15 |
| Sodium benzoate | 0.10 | 0.10 | 0.10 | 0.10 | 0.10 | 0.10 | 0.10 |
| Sodium citrate dihydrate | 0.20 | 0.20 | 0.20 | 0.20 | 0.20 | 0.20 | 0.20 |
| Citric acid | 0.22 | 0.22 | 0.22 | 0.22 | 0.22 | 0.22 | 0.22 |
| Sodium saccharin | 0.13 | 0.13 | 0.13 | 0 | 0 | 0 | 0.13 |
| Acesulfame Potassium | 0.080 | 0.080 | 0.080 | 0 | 0 | 0 | 0 |
| Sodium chloride | 0.50 | 0.50 | 0.50 | 0.50 | 0.50 | 0.50 | 0.50 |
| Dye | 0.0043 | 0.0043 | 0.0043 | 0.0043 | 0.0043 | 0.0043 | 0.0043 |
| Glycerin (96%) | 8.00 | 8.00 | 8.00 | 8.00 | 8.00 | 8.00 | 8.00 |
| Sorbitol (70%) | 13.15 | 13.15 | 13.15 | 13.15 | 13.15 | 13.15 | 13.15 |

|  | Example No. | | | | | | |
|---|---|---|---|---|---|---|---|
|  | 8 | 9 | 10 | 11 | 12 | 13 | 14 |
| Water | Q.S. | Q.S. | Q.S. | Q.S. | Q.S. | Q.S. | Q.S. |
| Propylene glycol | 23.02 | 23.02 | 23.02 | 23.02 | 23.02 | 23.02 | 23.02 |
| APAP | 2.00 | 2.00 | 2.00 | 2.00 | 2.00 | 2.00 | 2.00 |
| DXM | 0.062 | 0.062 | 0.062 | 0.062 | 0.062 | 0.062 | 0.062 |
| Doxylamine succinate | 0 | 0 | 0 | 0 | 0 | 0.038 | 0.038 |
| PE | 0.031 | 0.031 | 0.031 | 0.031 | 0.031 | 0.031 | 0.031 |
| Anise Flavoring with trans-Anethole | 0 | 0 | 0.055 | 0.11 | 0.21 | 0 | 0 |
| Dihydroanethole | 0.00025 | 0.00025 | 0 | 0 | 0 | 0.00025 | 0.00025 |
| Xanthan gum | 0.075 | 0 | 0.15 | 0.15 | 0.15 | 0 | 0 |
| 95% Ethanol (190 Proof) | 0 | 0 | 0 | 0 | 0 | 0 | 7.25 |
| Sodium benzoate | 0.10 | 0.10 | 0.10 | 0.10 | 0.10 | 0.10 | 0.10 |
| Sodium citrate dihydrate | 0.20 | 0.20 | 0.20 | 0.20 | 0.20 | 0.20 | 0.20 |
| Citric acid | 0.22 | 0.22 | 0.22 | 0.22 | 0.22 | 0.22 | 0.22 |
| Sodium saccharin | 0.13 | 0.13 | 0.13 | 0.13 | 0.13 | 0.13 | 0.10 |
| Acesulfame Potassium | 0 | 0 | 0 | 0 | 0 |  |  |

| -continued | | | | | | | |
|---|---|---|---|---|---|---|---|
| Sodium chloride | 0.50 | 0.50 | 0.50 | 0.50 | 0.50 | 0.50 | 0.50 |
| Dye | 0.0043 | 0.0043 | 0.0043 | 0.0043 | 0.0043 | 0.0043 | 0.0043 |
| Glycerin (96%) | 8.00 | 8.00 | 8.00 | 8.00 | 8.00 | 8.00 | 8.00 |
| Sorbitol (70%) | 13.15 | 13.15 | 13.15 | 13.15 | 13.15 | 13.15 | 13.15 |

Examples 1-14 were made according to the following procedure. DXM, APAP, and doxylamine succinate, if present, are added to propylene glycol by mixing at an appropriate speed for at least five minutes, if the actives are not dissolved after five minutes then the solution can be warmed slightly and stirred until the actives dissolve. An appropriate mixing speed means that the solution is mixed quickly but it does not splash out of the container. Next the flavor, which includes anise flavoring, trans-anethole, or dihydroanethole, is added to the solution and mixed for at least five minutes or until dispersed, whichever is later. Then, if alcohol is present, it is added as a solvent to form the glycol premix. If alcohol is not present, xanthan gum can be added to the solution and mixed, for no less than five minutes, until dispersed, to form the glycol premix.

Next, the glycol premix is added to the water. Then, the following components are added to the solution in the following order: the buffers, which include citric acid and sodium citrate, sodium benzoate, dye, sodium chloride, PE, and the sweeteners, which include sodium saccharin, acesulfame potassium, glycerin, and sorbitol. Each component is added and incorporated into the solution before the next component is added. The solution is mixed until all of the ingredients are dissolved and the solution is homogenous.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid medication comprising:
  a. from about 0.01% to about 0.04% phenylephrine, by weight of the composition;
  b. from about 1% to about 3% of a pain reliever, by weight of the composition, wherein the pain reliever is selected from the group consisting of acetaminophen, ibuprofen, ketoprofen, naproxen, aspirin, and combinations thereof; and
  c. from about 2 ppm to about 5 ppm of an anethole analog, by weight of the composition, wherein the anethole analog is selected from the group consisting of 1-methoxy-4-n-propylbenzene, methyl anisate, anisole, 2-chloroanethole, 2,6-dichloroanethole, 3-nitroanethole, 3,5-dinitroanethole, 3-cyanoanethole, 3,5-dicyanoanethole, 1-methoxy-3-(1-propenyl)benzene, and combinations thereof.

2. The liquid medication of claim 1 wherein the phenylephrine is phenylephrine hydrochloride.

3. The liquid medication of claim 2 further comprising from about 0.01% to about 0.2% of an antitussive, by weight of the composition, wherein the antitussive is selected from the group consisting of dextromethorphan HBr, chlophedianol, levodropropizine, and combinations thereof.

4. The liquid medication of claim 3 further comprising from about 3% to about 15% ethanol, by weight of the composition.

5. The liquid medication of claim 4 further comprising from about 3% to about 15% glycerin, by weight of the composition.

6. The liquid medication of claim 5 further comprising doxylamine succinate.

7. The liquid medication of claim 6 comprising from about 0.03% to about 0.05% doxylamine succinate, by weight of the composition.

8. The liquid medication of claim 5 further comprising guaifenesin.

9. The liquid medication of claim 5 wherein the anethole analog is 1-methoxy-4-n-propylbenzene.

10. The liquid medication of claim 5 wherein the anethole analog is 1-methoxy-3-(1-propenyl)benzene.

11. The liquid medication of claim 5 further comprising from about 0.01% to about 0.5% sucralose.

12. A liquid medication comprising:
  a. from about 0.01% to about 0.04% phenylephrine, by weight of the composition;
  b. from about from about 0.01% to about 0.2% dextromethorphan HBr; and
  c. from about 2 ppm to about 5 ppm of an anethole analog, by weight of the composition, wherein the anethole analog is selected from the group consisting of 1-methoxy-4-n-propylbenzene, methyl anisate, anisole, 2-chloroanethole, 2,6-dichloroanethole, 3-nitroanethole, 3,5-dinitroanethole, 3-cyanoanethole, 3,5-dicyanoanethole, 1-methoxy-3-(1-propenyl)benzene, and combinations thereof.

13. The liquid medication of claim 12 wherein the anethole analog is 1-methoxy-4-n-propylbenzene.

14. The liquid medication of claim 12 wherein the anethole analog is 1-methoxy-3-(1-propenyl)benzene.

15. The liquid medication of claim 12 wherein the liquid medication has a pH of about 2 to about 6.

16. The liquid medication of claim 12 further comprising from about 10% to about 35% propylene glycol.

* * * * *